(12) United States Patent
Yitzchaik et al.

(10) Patent No.: US 6,703,660 B2
(45) Date of Patent: Mar. 9, 2004

(54) HYBRID ELECTRICAL DEVICE WITH BIOLOGICAL COMPONENTS

(75) Inventors: Shlomo Yitzchaik, Jerusalem (IL); Joseph Shappir, Mevasseret Zion (IL); Micha Spira, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/933,873

(22) Filed: Aug. 22, 2001

(65) Prior Publication Data

US 2002/0050611 A1 May 2, 2002

Related U.S. Application Data

(63) Continuation-in-part of application No. PCT/IL00/00112, filed on Feb. 22, 2000.
(60) Provisional application No. 60/121,237, filed on Feb. 22, 1999.

(51) Int. Cl.[7] ............................................ H01L 29/758
(52) U.S. Cl. ...................................................... 257/315
(58) Field of Search .......................................... 257/315

(56) References Cited

U.S. PATENT DOCUMENTS

| 5,156,918 A | 10/1992 | Marks et al. |
| 5,721,131 A | 2/1998 | Rudolph et al. |
| 6,033,774 A | 3/2000 | Yitzchaik et al. |

OTHER PUBLICATIONS

Peter Fromherz, "Interfacing Neurons and Silicon by Electrical Induction", *Ber. Bunsenges. Phys. Chem.*, 1996, p. 1093–1102, vol. 100.

Richard S. Potember et al., "Conducting Networks from Cultured Cells on Self–Assembled Monolayers", *Synthetic Metals*, 1995, p. 1997–1999, vol. 71.

Mieko Matsuzawa et al., "Micropatterning of Neurons Using Organic Substrates in Culture", *Thin Solid Films*, 1997, p. 74–79, vol. 305.

Charles S. Dulcey et al., "Deep UV Photochemistry of Chemisorbed Monolayers: Patterned Coplanar Molecular Assemblies", *Science*, 1991, p. 551–554, vol. 252.

Rami Cohen et al., "Molecular Electronic Tuning of Si Surfaces", *Chemical Physics Letters*, 1997, p. 270–274, vol. 279.

Noemi Zenou et al., "Tuning the Electronic Properties of Silicon via Molecular Self–Assembly"in "Thin Organic Films", *ACS Symp. Ser.*, 1998, p. 57–66, vol. 695, Americal Chemical Society.

Shlomo Yitzchiak et al., "Chromophoric Self–Assembled Superlattices", *Acc. Chem. Res.*, 1996, p. 197–202, vol. 29, American Chemical Society.

N.A. Surplice et al., "A Critque of the Kelvin Method of Measuring Work Functions", *J. Phys. E: Sc. Instr.*, 1970, p. 477–482, vol. 3.

(List continued on next page.)

Primary Examiner—Fetsum Abraham
(74) Attorney, Agent, or Firm—Browdy and Neimark, P.L.L.C.

(57) ABSTRACT

The present invention concerns an electrical junction between one transistor and at least one voltage sensitive cell such as a neuron. The invention further concerns transistors to be used in said junction and methods for their preparation. By another aspect the invention concerns "an artificial chemical synapse" i.e. a junction between a cell, which secretes an agent, and a transistor bearing receptors for the agent, wherein binding of the agent to the receptor changes an electrical property off the transistor.

40 Claims, 8 Drawing Sheets

OTHER PUBLICATIONS

A. Offenhausser et al., "Neuron Cells Cultured on Modified Microelectronic Device Surfaces", *Journal of Vacuum Science & Technology,* 1995, p. 2606–2612, vol. 13, No. 5.

Alfred Stett et al., "Two–way Silicon–Neuron Interface by Electrical Induction", *Physical Review E,* 1997, p. 1779–1782, vol. 55, No. 2.

Peter Fromherz et al., "A Neuron–Silicon Junction: A Retzuis Cell of the Leech on an Insulated–Gate Field–Effect Transistor", *Science,* 1991, p. 1290–1293, vol. 252.

A. Offenhausser et al., "Neuron–Silicon Junction: Electrical Recordings from Neural Cells Cultured on Modified Microelectronic Device Surfaces", *Annual International Conference of the IEEE Engineering in Medicine and Biology Society,* 1997, p. 307–308.

A. Offenhausser et al., "Field–Effect Transistor Array for Monitoring Electrical Activity from Mammalian Neurons in Culture", *Biosensors & Bioelectronics,* 1997, p. 819–826, vol. 12, No. 8.

HYBRID ELECTRICAL DEVICE WITH BIOLOGICAL COMPONENTS

This is a continuation-in-part of co-pending parent International application No. PCT/IL00/00112, filed Feb. 22, 2000.

FIELD OF THE INVENTION

This invention is generally in the field of bio-molecular electronics, and relates to electrical devices with biological components.

BACKGROUND OF THE INVENTION

The following publications are believed to be relevant to the Background section of the specification.
1. Fromherz, P., "Interfacing Neurons and Silicon by Electrical Induction", *Ber. Bunsenges. Phys. Chem.*, 100:1093–1102 (1996).
2. Stett, A., Mÿller, B., Fromherz, P., "Two-way Neuron-Silicon Interface by Electrical Induction", *"Phys. Rev. B.,* 55:1779–1781 (1997).
3. Offenhaussser, A., et. al., "Neuronal Cells Cultured on Modified Microelectronic Device Surfaces", *J. Vac. Soc. Technol. A.,* 13(5):2606–2612 (1995).
4. Potomber, R. S., Matsuzawa, M., Leisi, P., "Conducting Networks from Cultured Cells on Self-assembled Monolayers", *Synthetic Metals",* 71, 1997 (1995).
5. Stett, A., Mÿller, B., Fromherz, P., "Two-way Neuron-Silicon Interface by Electrical Induction", *"Phys. Rev. B.,* 55:1779–1781 (1997).
6. Matsuzawa, M., Umemura, K., Beyer, D., Sugioka, K., Knoll, W., "Micropatterning of Neurons using Organic Substances in Culture", *Thin Solid Films,* 305:74–79 (1997).
7. Dulcey, C. S., Georger, J. H., Krauthamer, V., Stenger, D. A., Fare, T. L., Calvert, J. M., *Science,* 252:551 (1991).
8. (a) Cohen, R., Zenou, N., Cahen, D., Yitchaik, S., "Molecular Electronic Tuning of Si Surfaces" *Chem. Phys. Lett.,* 279:270–274 (1997);
(b) Zenou, N., Zelichenok, A., Yitzchaik, S., Cohen, R., Cahen, D., "Tuning the electronic properties of silicon via molecular self-assembly" in "Thin Organic Films", C. W. Frank—Ed, *ACS Symp. Ser.,* 695:57–66 (1998).
9. Yitzchaik, S., Marks, T. J., "Chromophoric Self-Assembled Superlattices", *Acc. Chem. Res.,* 29:197–202 (1996) and references therein.
10. 08/857,769 of May 1997.
11. U.S. Pat. No. 5,156,918.
12. Surplice, N. A.; D'Archy, R. J. J. Phys. E: Sc. Instr. 1970, 3, 477–482.

Interaction between neurons and electronic devices have been in existence for several decades for a plurality of purposes. During the past decades, these interactions were usually achieved by inserting an electrode or an array of electrodes into the neurons or placing an electrode or an array of electrodes in the vicinity of the neurons' membranes so as to detect voltage changes. The detection electrode or array of electrodes can also be used for the stimulation of neurons.

With the growing body of knowledge concerning transistors and semi-conductors there have been several attempts directed at the coupling the two types of information flow: electron conduction in solids (achieved by the transistor), and ion conduction in aqueous environments (carried out by the neurons). However, the coupling between the transistors and the neurons suffered from a series of problems including basic scientific problems as well as technological difficulties. Direct coupling of neurons to enhancement type MOS transistors requires the application of a DC bias between the biological solution and the transistor substrate in order to create a conducting channel. The combination of the DC bias, the biological ionic solution and the transistor, is a potential source for a series of degradation processes resulting from leakage currents, heat generation, electrochemical corrosion and ionic drift instabilities. All this will eventually lead to damage of the neuron and/or the transistor.

The publication of Stett et al. (Ref. 2) describes a nerve cell which is placed on a combined microstructure of an insulated spot of doped silicon and an insulated-gate field effect transistor. The neuron was placed on the transistor without any adhesive material. Voltage pulses are applied by the insulated spot to the neuron through capacitive coupling. They elicit neuronal activity which in turn can be detected by the transistor. The article describes a bi-directional interface between the ionics of the neuron and the electronics of the silicon, achieved by two separate modalities. Here, however two separate locations on the silicon chip spaced-apart in a horizontal plane are used, namely, one for sensing of neuronal activity achieved by an insulated-gate field effect transistor, and the other for capacitive simulation of neuron activity achieved by an insulated spot of doped silicon. This approach of two separate locations, one for the neuron activation and one for sensing its activity, imposes several limitations in multi neuron multi transistor systems, as follows:

it requires accurate positioning of each neuron on the electronic circuit;

it increases the number of electronic connections to a given neuron system; and it requires larger area of the electronic system.

It is highly desirable to provide coupling between neurons, (and other voltage sensitive cells) and electrical devices both for the purpose of detecting electrical activity in these cells, and for stimulating the cells via said electrical devices. The coupling should be such which allows the detection and stimulation by use of a relatively simple electronic structure, and in addition, the electrical structure should be bio-compatible and the mode of its coupling should be such as not to produce the electrochemical changes and toxic substances which are harmful to live cells.

The term "chemical synapses", refers to a junction between two neurons wherein the axon terminals of a pre-synaptic cell, containing a vesicle filled with a particular neurotransmitter substance, are in close vicinity to the membranes of a post synaptic cell. When the nerve impulse reaches the axon terminal the vesicles are exocytosed releasing their neurotransmitter components into the synaptic cleft which is the narrow space between the pre-synaptic and the post synaptic cell. The transmitter diffuses across the synaptic cleft, and then binds to receptors on the post synaptic cells. Upon binding, the neurontransmitter induces a change in the ionic permeability of the post synaptic membrane that results in the disturbance of the electrical potential at this point. If the electrical disturbance is sufficiently high it can induce an action potential, or a muscle contraction (where the cell is a muscle), or alternatively, may be sufficient to trigger release of hormones from gland cells.

Although the chemical synapse site is a major component in the modulation of neuronal activity, said modulation effecting properties such as memory, learning, degradation due to various neurodegenerative diseases, the physiological phenomena of the synapse was studied and utilized mainly in biological systems.

Possible means for communication between nerve cells and transistors may be polarizable molecules. Such molecules are described in Ref. 9. Furthermore, U.S. patent application Ser. No. 08/857,769, May 1997, and U.S. Pat. No. 5,156,918 concern methods for forming a polymeric structure composed of two or more discrete monolayers wherein at least one layer is composed of polycyclic aromatic molecules with a defined Z-axis oriented substantially normal to the plane or at an angle close to normal, up to ca. 45°. Ref. 8 further addresses the effects of polarizable molecules on the electronic properties of silicon.

Glossary

"Voltage sensitive cell (VSC)"—a cell in which normal physiological activity is modulated by voltage changes across its membrane. Typical examples are neurons, muscle cells and cells of glands which secrete hormones as a result of voltage change.

"Electrical junction"—a functional connection between a single transistor and at least one VSC enabling signal transfer in at least one direction, either from the transistor to the VSC, or from the VSC to the transistor through capacitive coupling.

"DC bias"—the voltage applied between the biological solution in which the VSC is embedded and the transistor substrate, which sets the transistor ready for sensing the VSC activity (i.e., "opens" the transistor).

"External surface of the transistor"—the outer surface of an uppermost, insulating layer covering the active component of the transistor.

"Binding moieties"—refers to molecules which may be of a biological or non-biological origin which can bind to components present on the membrane of the VSC. By a preferred embodiment, the moieties form together with components present on the membrane of the VSC, "a specific pair-forming group" (see below). For example, where the membranal component is an antigenic epitope, the binding moiety is an antibody, where the membranal component is a receptor, the binding moiety is its specific ligand, or an adhesion moiety capable of "affinity binding" (see below) thereto, where the membranal component is a glycoprotein, the binding moiety is a lectin, etc. By other embodiments, the binding of the binding moieties to the membranal component is by non-affinity bindings such as by hydrophobic interactions due to hydrogen bonds or due to van der-Wallace interactions. It should be noted that this term does not necessarily refer to the full molecule which interacts with the VSCs membranal component, and may only refer to the region of the full molecule which binds to said membranal component. For example, where the membranal component is a receptor, the binding moiety may be only a sequence of the adhesion molecule which specifically binds to said receptor.

"A specific pair forming group"—two biological molecules which are capable of affinity binding (see below) to each other. Each member of the group is capable of identifying and interacting with its specific counter partner form among similar molecules of other species. For example, if a pair forming group is an antibody and its specific antigen, then the antibody is capable of specifically discriminating and interacting with the specific antigen, while not interacting with similar antigens present in the environment.

"Affinity binding"—refers to the specific non-covalent interaction between two members of a specific pair forming group.

"Hyper-polarizable chromophores"—are typically aromatic molecules characterized in that that they contain an electron donating moiety, an electron withdrawing moiety separated by a $\pi$-bridge. The family includes also chromophores with high field polarization properties, i.e. nth order hyper-polarizable chromophores. They are sometimes referred to as voltage sensitive dyes which have a positively charged chromophore and a negatively charged counter-ion which is ionically bound to the chromophore. The classical voltage-sensitive dye respond to voltage pulses by electrochromism, i.e. upon excitation, the molecules undergoes a shift of the positive pole. In a hyper-polyrizable chromophore, an electrical excitation from an action potential of a nerve cell modulates the distribution of the $\pi$-electrons, i.e. the charge distribution along the molecule which leads to a large change in the dipole moment of the molecule. Both, the anion flipping and the change in the dipole moment effect the transistor to which these hyper-polarizable chromophores are attached.

"Floating gate"—an insulated electrode of a MOS transistor on which an electric field is applied, thereby inducing an electric field to the active component of the transistor through capacitive coupling.

"Depletion type device"—an insulated-gate field-effect transistor in which free carriers are present in the channel (active component) when the gate-source voltage is zero. Channel conductivity thus exists at zero voltage between gate and source and is controlled by changing the magnitude and polarity of the gate voltage. A depletion type device is normally-on. For the normally-on depletion device, a current can flow at a zero gate potential, and the current can be increased or decreased by varying the gate voltage.

"Spacer"—A molecule or group of molecules used to bridge the gap between the surface of the transistor and the VSC so as to minimize the "shunt" caused by the electrolyte containing solution. The spacers of the present invention may be attached to hyper-polarized chromophores so as to bridge the varying distances between the surface of the transistor and the VSC so that when the electrical junction is formed, the space between the surface of the transistor and the uneven surface of the membrane of the VSC is bridged by the spacer and the conjugated hyper-polarizable chromophore, notwithstanding the fact that the membrane itself is uneven so that the spacer has varying dimensions at different regions. The spacers may also be used to place the binding moieties at varying distances from the transistor surface so that the binding moiety may bind to membranal components on the VSC notwithstanding that its components are at varying distances from the surface of the transistor.

By another alternative, the spacer may be used by itself so as to simply "close" the gap between the surface of the transistor and the VSC so as to minimize the shunt. Typically, the length of the spacer ranges from 1 nm to 30 nm. Typically the spacer should be any inert molecule such as oligosaccharides, straight hydrocarbons, branched hydrocarbons, peptides, etc. A spacer may also be a combination of one of the above-mentioned inert molecules bound to a hyper-polarizable molecule. Alternatively, the spacer may be made of multi-layers of chromophores or dendritic structures of chromophores, thus the spacer is an "active" component.

"Agent secreting cell"—a cell which normal biological, activity is secretion of agents to the extracellular environment. Examples of agent secreting cells are neurons which secrete neurotransmitters, gland cells which secrete hormones and the like.

"Agent secreting region of the cell"—the region of the agent secreting cells from which the agent is secreted. Where the agent secreting cell is a neuron, this region is the pre-synaptic region.

"Electrochemical junction"—refers to a functional connection between an agent secreting cell and a transistor. The agent secreting cell should be positioned in such an orientation so that the agent secreted therefrom can reach the transistor. While by one embodiment the orientation may be adjacent positioning, such as in a chemical synapse where the cells and the transistor are adjacent, by other embodiments the orientation may be non-adjacent, for example, if the transistor is placed inside a body, and the blood circulation may bring agent secreted from the agent secreting cell present at a distanced location to the transistor. The transistor has immobilized thereon recognition moieties which are capable of affinity binding to the secreted agent. The affinity binding between the recognition moiety and the agent causes a change of at least one electrochemical property of the transistor such as capacitance.

"Recognition moieties"—biological molecules capable of forming a specific pair forming group with the secreted agent. Typically, where the secreted agent is a neurotransmitter or a hormone, the recognition moieties are the receptors for the neurotransmitter or the hormone, respectively.

"Catalytic moieties"—molecules having an activity which discontinue the affinity binding between the recognition molecule and the agent, for example, by degradation of the agent.

SUMMARY OF THE INVENTION

By one of its aspects, the present invention concerns an electrical junction between a single transistor and at least one voltage sensitive cell (VSC). The electrical junction of the invention typically shows at least one of the following advantageous characteristics:

It enables bi-directional voltage transfer between the transistor and the VSC. This means, that by utilization of a single transistor, it is possible both to detect voltage changes from the VSC (for example to detect neuronal activity in neurons) and using the same modality also to stimulate the VSC by capacitance changes of voltage. In this case, the transistor is a floating gate depletion type device, and the VSC is associated with the floating gate and is capable of being stimulated by a voltage pulse applied to the source, channel and drain of the transistor.

When using the transistor in the form of a depletion type device in the junction of the present invention, it can also be characterized in that it does not need a DC bias to be applied between the transistor and the solution containing the VSC. This means, that the VSC is not under a constant stimulation by a DC voltage application. Typically, living cells deteriorate after a prolong application of voltage to their members, and thus an electrical junction without a DC voltage bias enables to maintain the VSC in a viable form for prolonged periods of time.

The omission of the DC bias means also that there is significantly less risk for electrochemical corrosion of the transistor through reaction with the ionic biological solution.

By another characterizing property the electrical junction of the invention enables the anchoring of the VSC to the external surface of the transistor by binding moieties, which are conjugated at one end to the external surface of the transistor, and at the other end are capable of affinity binding with membranal component on the VSC membrane. These binding moieties significantly decrease the size of the cleft between the membrane of the VSC and the external surface of the transistor, thus minimizing the "shunt" of the electrical caused by the aqueous solution present in said cleft. Optionally, the closure of the "shunt" may be improved by use of spacers.

Another possible characterizing feature of the electrical junction of the invention is that the voltage transfer between the membrane of the VSC and the external surface of the transistor, in both directions, is mediated by hyperpolarizable chromophore.

Thus, the present invention concerns an electrical junction between one transistor and at least one voltage-sensitive cell (VSC) characterized by at least one of the features selected from the group consisting of:

(i) voltage transfer between the transistor and the VSC is bi-directional, the transistor being a floating gate depletion type device, the VSC being associated with the floating gate and being capable of being stimulated by a voltage pulse applied to the source, channel and drain of the transistor;

(ii) there is no DC bias between the transistor and the solution containing the VSC, the transistor being a depletion type device;

(iii) the VSC is anchored to the external surface of the transistor by binding moieties, optionally through spacers;

(iv) the voltage transfer between the membrane of the VSC and the external surface of the transistor, and between the external surface of the transistor and the membrane of the VSC is mediated by a hyperpolarizable chromophore;

(v) a combination of two or more of the features of (i) to (iv).

The electrical junction of the invention enables through formation of a transistor neuron hybrid the coupling between electrical devices and voltage sensitive cells (neurons, muscle cells and gland cells) for various utilities as follows:

(1) It may be used as an in vivo sensor in order to detect electrical activity in voltage sensitive cells, (such as neurons);

(2) It may be used in vivo in order to stimulate nerve cells or muscle cells, for example for stimulation of muscle cells of paralyzed limbs in order to achieve some sort of movement of the muscles even if they do not receive neuronal input from motor neurons;

(3) It may be used both for detection of neuronal pulses and stimulate of voltage sensitive cells. For example where a neuron or muscle activated prosthesis is used. In such a case, it is necessary to stimulate nerve cells or the muscle cells in order to produce movement in the prosthesis. And in addition it may be desirable to record from other nerve cells or muscle cells in order to receive a feedback information concerning the position, and movement thereof in order to enable coordinated movements and correction of mistakes and this enabling smooth movement of the prosthesis.

(4) The transistor-neuron hybrid may be used in various artificial sensing devices, such as devices which have an ability to sense light ("artificial eye") or sound ("artificial ear"). This will enable to activate regions of the central nervous system connected to sight or hearing by stimulating these regions with light or sound input obtained from electrical devices (such as a camera or a microphone) so as to enable processing of the artificially produced information by the central nervous system. The transistor-neuron hybrid may be used to record impulses from sensing organs themselves (the eye or the ear) and transfer the electrical output to electrical devices, such as computers, capable of processing the information, for example, in cases where the sensing organ (eye) is functional but the visual cortex region which should have processed the visual information is impaired.

(5) By another option, the transistor-neuron hybrid will enable the creation of a "brain-computer" hybrid structure which will enable new breakthroughs in calculation and intelligence processing using both the computational power of an electrical computer and the flexibility and adjustability properties of a biological central nervous system.

As indicated above, the bi-directional voltage transfer between the VSC and the transistor is achieved by the use of a depletion type transistor with floating gate for both the neuron sensing and stimulation purposes. The depletion type doping level is such that the application of voltage required for the stimulation of the VSC, will not deplete the channel. This doping level is calculated by the use of the well known equation describing the relation between junction depletion layer charge and the applied voltage. If minimum channel length device is used, it may be possible to obtain even higher stimulation voltages. This is due to lateral bridging of the source and drain depletion layers, thus screening the depletion type channel from the substrate.

The use of a floating gate configuration eliminates the sensitivity of the transistor output signal to the exact location of the VSC on the MOS channel, leading to significantly narrower distribution of the signals that have to be detected.

It should be clear that bi-direction signal transfer utilizes the same location on a semiconductor device (a single transistor) for both the stimulation and the sensing. However, two locally adjacent identical transistors can be utilized with the same VSC, one for stimulation and the second for sensing. The use of a depletion type transistor, which is normally-on, enables to eliminate the need for any DC bias between the transistor and the solution containing the VSC. Thus, electrical signal coming from the VSC through the binding moieties induces a gate voltage which affects the surface potential of the active component, thereby increasing or decreasing a current passing the active component between source and drain electrodes. The transistor thereby serving as a sensor. To stimulate the VSC activity, the source is disconnected from its supply, and the neuron stimulation voltage is applied to the drain. As a result, the source, channel and drain will be at the same voltage and through the capacitive coupling to the floating gate and the neuron, will activate the letter. It should be mentioned that the roles of the source and drain can be exchanged in the stimulation process.

The switching of the source and drain during the stimulation process may be performed by utilizing two transistors, each of regular enhancement type, on both sides of the depletion type transistor. These regular type transistors are associated with the source and drain, respectively, of the depletion type transistor.

The neuron sensing and stimulation processes can be achieved in a device including the electrical junction between a floating gate depletion type transistor and a VSC, and an additional switching transistor connected to the gate of the floating gate depletion type transistor. In such a device, the neuron stimulation is carried out by supplying voltage to the gate of the switching transistor.

Thus, according to another aspect of the present invention, there is provided a device for selectively detecting voltage changes from a VSC and transferring voltage changes to the VSC, the device comprising:

an electrical junction between a floating gate depletion type transistor and the VSC, which is associated with the floating gate and is capable of being stimulated by a voltage pulse applied to the gate of the floating gate transistor; and a switching transistor connected by either one of its source and drain electrodes to the gate of said floating gate transistor to apply said voltage pulse by supplying voltage to a gate of the switching transistor.

The transistor structure is provided with an additional electrostatic screening layer, e.g., gold layer, which covers the entire circuit area except for openings above the floating gates. This enables to reduce noise to such low levels that will enable reliable detection of the neuron signals on one hand and prevent unintended activation of the VSC on the other hand. Furthermore, the existence of the screening which is kept at the potential of the biological solution, further reduces the risk of electrochemical corrosion processes.

The anchoring of the VSC to the external surface of the transistor can be achieved by a plurality of binding moieties such as antibodies, receptors, ligands, lectins and adhesion molecules. Where the VSC is a neuron, typically the biological binding molecules are adhesion molecules such as small molecular weight peptides derived from the neurite promoting domains of laminine (an extracellular matrix) protein) and in particular two well studied synthetic peptides, 8 and 10 amino-acids each having the following sequences:

Lys-Val-Ala-Val-Ser-Ala-Asp-Arg; and

Cys-Ser-Arg-Ala-Arg-Lys-Gin-Ala-Ala-Ser; [PA 22-2 and P20-GC—Ref.6].

Where the VSC is a neuron, the binding moieties may be used not only to anchor the VSC to the surface of the transistor, but also to direct the growth of the neuron to the proper location in the transistor, and repulse its growth from an undesired location. This regulated growth may be achieved by conjugating to the surface of the transistor alternating micro strips of growth promoting molecules such as polylysines, and growth repulsive molecules such as collapsin. These micro strips will ensure that the actin-based motality of the growth will be directed to the desired location on the surface of the transistor.

The voltage transfer between the membrane of the VSC and the external surface of the transmitter may be mediated by hyper-polarizable chromophores. These chromophores are very sensitive to the electrical signals of a nerve cell where such signals cause a charge in the dipole moment and charge density distribution in these chromophores. These changes cause a change in the surface potential of the transistor to which these chromophores are attached.

By a preferred embodiment the electrical junction of the invention features all of the above characteristics, i.e. it enables bi-directional voltage transfer between the VSC and the transistor with no DC bias between the two; the VSC is anchored to the surface of the transistor by biological binding moieties; and the voltage transfer in both direction is mediated by voltage sensitive dye.

By a preferred embodiment the transistor of the junction utilizes silicon-based integrated technology, but may alternatively utilize any other semiconductor structure, e.g. GaAs-based.

By another aspect of the present invention, the invention concerns an array of at least two electrical junctions. Each electrical junction may be designed as described above, namely a single transistor for a single neuron. Alternatively, at least two locally adjacent transistors may be associated with a common neuron, in which case one of the transistors may serve for VSC stimulation, and the other for sensing purposes.

By another aspect, the invention concerns a hybrid electronic device comprising the junction of the invention. The transistor is a depletion type device with a floating gate capacitance coupled to a VSC. A power supply maintains potential difference between source and drain electrodes. By maintaining this potential difference constant, the transistor operates as a sensor for detecting signals coming from the VSC through the current changes caused by this coming signal. By replacing this potential difference by a high voltage applied to the source, channel, and drain of the transistor; it acts as a stimulator of the VSC activity. Preferably, an additional metal layer is used for screening purposes. Selective-sites for the neurons are provided by proper openings in the screening metal layer and by using controlled substrate-neuron linking chemistry.

Thus, the present invention provides an advanced MOS-FET structure, which has larger tolerance for the placement of the VSC over the MOS-FET device by using floating gate devices, eliminates the need for DC bias by using depletion type devices, and reduces the noise level as well as minimize corrosion processes by a screening technique and selective-sites for the neurons, using controlled substrate-neuron linking chemistry.

The device of the invention may also be used to detect voltage changes from a plurality of VSC and/or to transfer voltage changes to a plurality of VSCs and in that case it should comprise the array of the invention wherein each transistor in the array is electrically coupled as described above.

By another embodiment the transistor may have immobilized on its external surface by binding moieties as described above. The transistor may also have immobilized on its external surface various growth promoting and growth repulsive molecules, such as those described above in order to regulate the growth of the VSC, and notably the neuron only to regions of the transistor wherein electrical coupling is desired.

Alternatively, or in addition to having immobilized thereon-binding moieties, the transistor of the invention may have immobilized thereon hyper-polarizable chromophores. The attachment is done by chemical reaction on the outer layer of the transistor forming monolayer multi-layers or dendrimers of polarizable chromophores with polar ordering (all the di-poles are pointed either toward or away from the surface).

Since the surface of the VSC is not smooth, the space between said surface and the flat surface of the transistor is irregular. In order to decrease to a minimum the "shunt" produced by the electrolyte-containing solution present in that space, it is desired to partially seal that space. Therefore, it is desired to attach either to the hyper-polarizable chromophore, or to the binding moieties on spaces of varying length, or alternatively, produce hyper-polarizable chromophores of varying length so that not withstanding the fact that some regions of the VSC membrane are at different distances from the transistor surface, essentially all these distances are bridged by the spacer and the hyper-polarizable chromophore; spacer and binding moiety; or hyper-polarizable chromophores of varying lengths. Alternatively, the spacers may be used by itself to close the gap, i.e. without any binding moieties of hyper-polarizable chromophores provide a closure of the cleft.

Typically, the length of the spacer should vary from about between 1 nm to 30 nm.

The spacers may be constructed in a "tree like" form wherein various "branches" of the tree are at varying lengths from the surface of the transistor. Alternatively, the spacers or the varying length hyper-polarizable chromophores may be positioned as essentially straight molecules of varying length arranged at a spatial arrangement so that in each region there are a plurality of spacers or hyper-polarizable chromophores of different lengths. Examples of molecules which are suitable to be used as spacers are inert molecules terminated with chemical functionality capable of anchoring polarizable chromophores, e.g. alkylhalide, benzylhalide, acylhalide, amine, active ester, etc., oligosaccharides, straight or branched hydrocarbon molecules, polymers, poly (4-vinylpyridine) and poly (4-chloromethylstyrene).

By a third aspect, the present invention concerns methods for the production of any one of the above transistors.

By one embodiment, the method for the production of a transistor utilizing fabrication of a MOS-FET device in a semiconductor substrate, wherein the external surface of said device is patterned to define selective sites for at least one VSC, said sites being displaced in a horizontal plane with respect to a location of an active component of the device.

By another aspect the present invention concerns an electrochemical junction between a cell which secretes an agent and a transistor. This electro-chemical junction is in fact "artificial chemical synapse" wherein the pre-synaptic region is of a live biological secreting cell, while the "post synaptic" region is a transistor. The principle of the artificial chemical synapse is that the post synaptic transistor bears on its surface recognition moieties, such as receptors which are capable of binding of the secreted agent. The binding of the agent to the recognition moiety changes at least one electrical property of the transistor which can be measured. Typically, the electrical property is changed di-pole moment of the recognition moiety which changes as a result of the secreted agent. Alternatively, or in addition, the change in electrical property may be a change in capacitance of the molecules pressed on the surface of the transistor.

The electrochemical junction of the invention, also comprises a catalytic moiety, such as an enzyme which can terminate that binding between the secreted agent and its recognition moiety. For example, where the catalytic moiety is an enzyme capable of degradation of the secreted agent, it will quickly eliminate the secreted agents present in the space between the agent secreting cell and the surface of the transmitter, and thus shift the equilibrium of the binding of the agent to its recognition, so that the agents are detached from the recognition moiety and subsequently also degradation. This catalytic activity enables to "initialize" or "regenerate" the transistor very quickly back to a situation where its recognition moieties are unbound and thus capable of sensing other concentrations of secreted agents. The catalytic moiety in fact enable to monitor essentially "on-line" fluctuations in the concentration or presence of the secreted agent in the sample.

Thus, the present invention concerns an electrochemical junction between an agent-secreting cell and a transistor comprising:

the agent-secreting region of the cell positioned at an orientation enabling transfer of the agent to a location on the surface of the transistor, said location having immobilized thereon recognition moieties capable of affinity binding to said agents; said binding between the recognition moiety and the agent causing the modulation of at least one electrochemical property of the transistor; said location further comprising catalytic moieties capable of degradation of said agent.

Where the agent secreting cell is a neuron, the secreted agent is a neurotransmitter and the agent secreting region of the cell is a pre-synaptic region of the neuron. The orientation of the agent secreting region in respect to the transistor should be either such which enables transfer due to the fact that the two are adjacent, or alternatively, they may be distanced from each other and the circulation such the blood may bring the secreted agent into the vicinity of the transistor.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

I. Electronics

Figure 1:
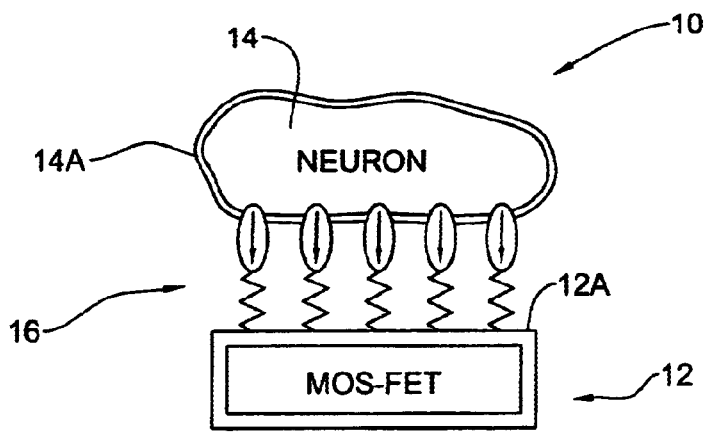
FIG. 1 schematically illustrates the main constructional parts a hybrid device according to the invention.
Figure 2A:
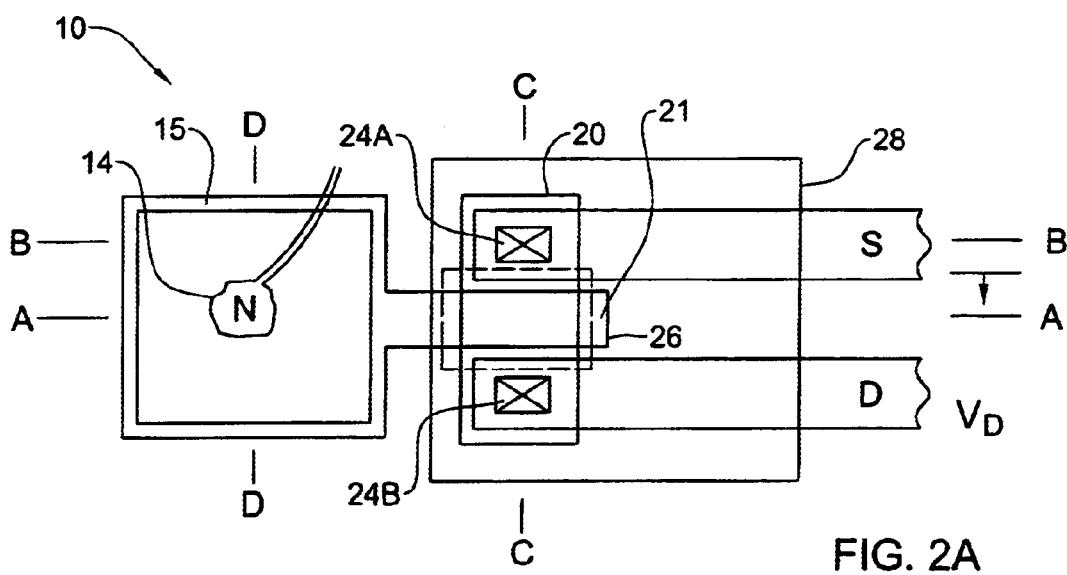
FIG. 2A is a top view of the hybrid device of the present invention, more specifically illustrating the components of a MOS-FET structure.
Figure 2B:
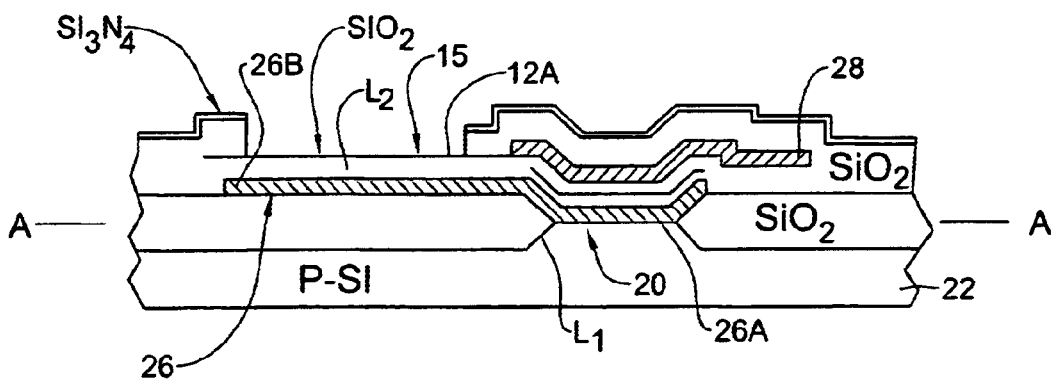
FIGS. 2B to 2E cross sections of the device of FIG. 2B, taken along lies A—A, B—B, C—C and D—D, respectively.
Figure 2C:
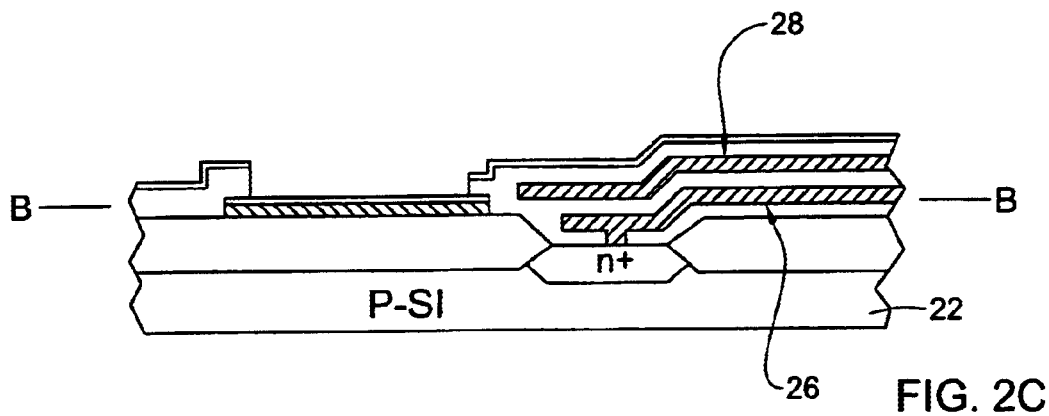
Figure 2D:
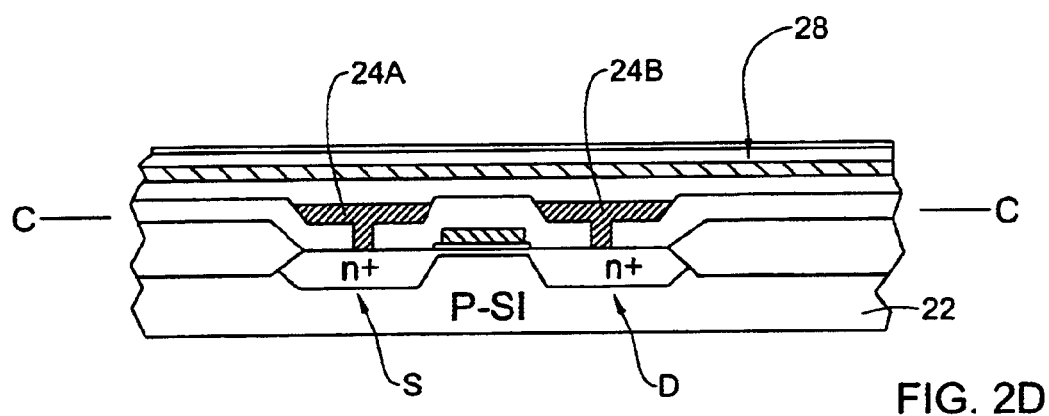
Figure 2E:
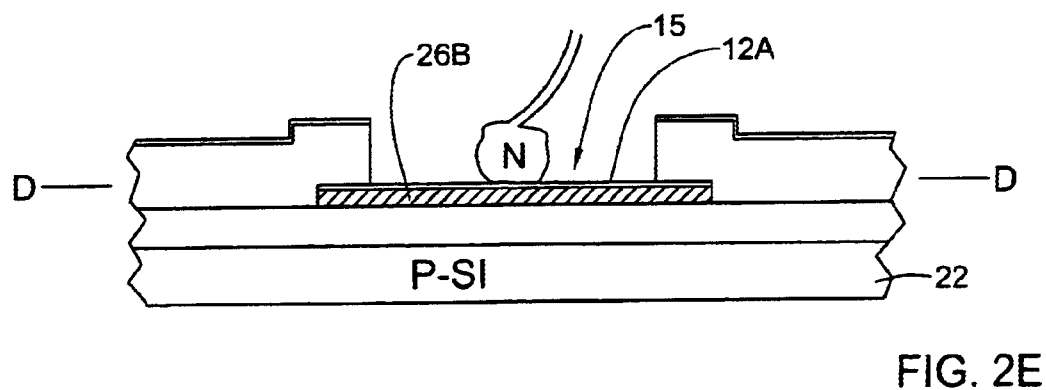

Referring to FIG. 1, there is illustrated a hybrid device 10 according to the invention. The device 10 is composed of a MOS-FET structure 12 coupled to a neuron 14 (constituting a VSC) through binding moieties 16. The operation of the device 10 presents an electrical junction between an active component (not shown here) of the transistor 12 and the neuron 14. Biological binding moieties 16 serve for anchoring the VSC 14 to the external surface 12A of the transistor structure 12. To this end, binding moieties 16 are conjugated at one end to the external surface of the transistor, and at the other end are capable affinity binding with a membranal component on the VSC membrane 14A, as will be described more specifically further below.

FIGS. 2A–2E show more specifically the relative disposition of the constructional elements of the device 10. The transistor structure 12 is a floating gate, depletion type device. An active component 20 with a channel implant 21 is formed in a semiconductor (e.g., Si) substrate 22, and source and drain electrodes 24A and 24B make contacts to the active component 20. The active component of the depletion type device is typically a semiconductor structure having at least one conducting zone (or layer), and is manufactured by integrated circuits technology. A floating gate 26 is typically an insulated electrode, insulated from the active component by a thin insulating layer $L_1$ (e.g., $SiO_2$) and insulated from the neuron by another insulating layer $L_2$, whose outer surface presents an external surface 12A of the device to which the neuron 14 is coupled.

As clearly seen in the figures, the floating gate 26 is shaped such as to have its one portion 26A located in the vicinity of the active area 20, and by its other portion 26B located outside the active area underneath a neuron site 15. This design enables to displace the neuron site from the active area, thereby increasing signal-to-noise ratio of the device operation. Additionally, this enables to locate a screening metal layer 28 above the active area. This increases even more the signal-to-noise ratio.

Figure 3A:
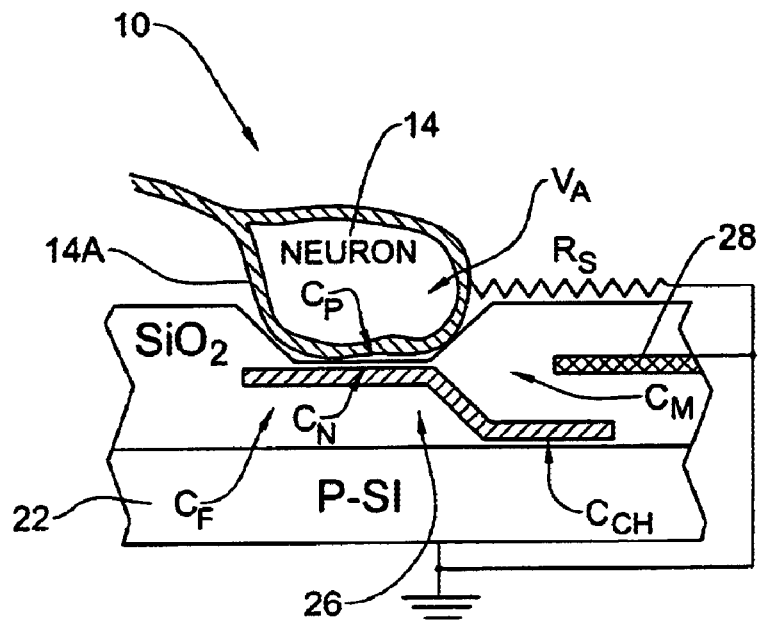
FIGS. 3A and 3B schematically illustrate main operational principles of the device of FIG. 2A.
Figure 3B:
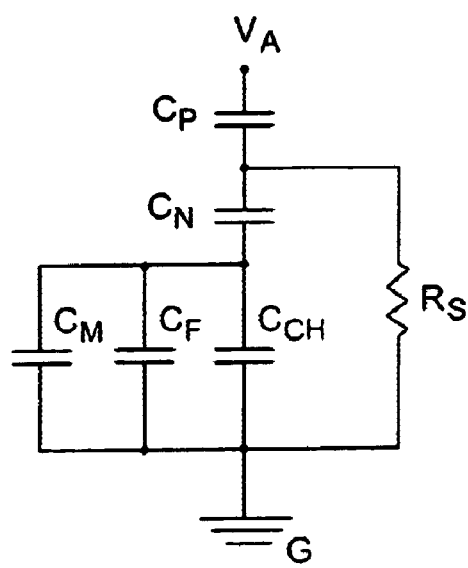

Turning now to FIGS. 3A and 3B, there is shown that the hybrid device 10 presents an electrical circuit of five capacitance, wherein $C_{ch}$ is the channel gate capacitance, $C_F$ is the overlapping capacitance of the floating gate and the semiconductor substrate over thick oxide layer, $C_M$ is the capacitance between the floating gate and the grounding shield (screening electrode), $C_N$ is the capacitance between the neuron membrane and the floating gate, $C_P$ is the capacitance of the neuron membrane portion with the area equal to that of $C_N$, $R_S$ is a solution shunting resistance.

The device 10 operates in the following manner. At a sensing operational stage, a certain constant small potential difference of about 0.1V is maintained between the source and drain of the transistor, thereby providing direct current flowing through the active component. Once the neuron is stimulated, its action potential affects the polarization of binding molecules, which in turn induces an electric field affecting the surface potential of the active component, thereby causing changes in the current, which can be detected. At a stimulating stage, the source is disconnected from the external circuit, i.e. is floating, and the stimulation voltage is applied to the drain. Under these conditions, the source, channel and drain, all receive the same stimulating voltage. Through the floating gate capacitive coupling and the induced changes in the molecular polarization, the neuron is stimulated.

Typical values for the different areas, oxide thicknesses and capacitance values are presented in Table I below. Also given in the table is the capacitance $C_P$ of the neuron membrane. It is based on the assumption of about 50 Å neuron membrane thickness and a dielectric constant of about 2. The $SiO_2$ dielectric constant is 3.9.

TABLE I

|  | A[$\mu m^2$] | t[Å] | C[fF] |
|---|---|---|---|
| $C_{ch}$ | 4 | 500 | 3 |
| $C_F$ | 60 | 10,000 | 2 |
| $C_M$ | 10 | 10,000 | 0.035 |
| $C_N$ | 25 | 100 | 90 |
| $C_P$ | 25 | □50 | 88 |

The correlation between the floating gate potential $V_{FG}$ and neuron action potential at the onset of $V_A$ is given by:

$$V_{FG} = \frac{C_S}{C_S + C_{Ch} + C_F + C_M} V_A \approx 0.9 V_A$$

where $C_S$ is the series connection of $C_N$ and $C_P$ for the values of Table I; and $V_{FG}=0.47V_A$. Assuming $V_A=90$ mV, one obtains that the floating gate voltage, is $V_{FG}=81$ mV.

The MOS device will be of the n-channel depletion type obtained by implanting arsenic in the channel with a dose of $10^{12}$ cm$^2$. To a first order approximation, the stand-by current $i_0$ in the device is given by:

$$i_0 = \frac{W}{L} q - n_0 \mu_e V_{DS}$$

Assuming the following:

$$\frac{W}{L} = \frac{2 \, \mu m}{2 \, \mu m}; \quad V_{DS} = 1 \text{ V and } \mu_e \approx 500 \text{ cm}^3/\text{V} \cdot \text{sec}$$

we obtain that the stand-by current is: $i_0 = 8 \, \mu A$.

The application of voltage signal—$V_{FG}$ to the floating gate will cause a current signal in the MOS transistor given by:

$$i_s = \frac{W}{L} C o x \mu_e V_{FG} V_{DS}$$

Substituting:

$$V_{FG} = 81 mV$$

we obtain that $i_s = 2.9 \, \mu A$.

This is the current signal obtained when the neuron is activated in the case of strong coupling. The shunting resistance of the ionic solution will cause the decay of $i_s$ with a time constant of:

$$\tau = R_S (C_S + C_{Ch} + C_F + C_M)$$

$R_S$ varies with the distance d of the neuron from the top oxide. Assuming d=100 Å and a solution resistivity of 1000 Ω·cm, one obtains:

$$R_S = \frac{W}{L \cdot d} \rho = \frac{\rho}{d} = 10^9 \, \Omega$$

and consequently $\tau=50 \, \mu sec$. As will be explained further below, the addition of the molecular amplifiers will not only increase the signal level, but will increase also $R_S$ and $\tau$, thus eliminating the effect of RC on the detected signal.

There are three sources of noise in the device:
Thermal noise:

$$\langle V_n^2 \rangle = 4kTB \cdot R, \quad \langle i_n^2 \rangle = \frac{4kTB}{R}$$

Here, B is the bandwidth assumed to be approximately 20 KHz, based on the fact that the neural signals have milliseconds time constants; R is the channel resistance.

Assuming a device with the channel width W and length L as follows:

$W=L=2$ mm, $\mu_e \approx 500$ cm$^2$/Vsec, $n_0=10^{12}$ cm$^{-2}$ and $kT=0.026$ eV, $q=1.6 \cdot 10^{-19} C$ $$R = \frac{1}{500 \cdot 1.6 \cdot 10^{-19} \cdot 10^{12}} = 62.5 \text{ k}\Omega$$

$$\langle i_n^2 \rangle = \frac{4 \cdot 0.026 \cdot 1.6 \cdot 10^{-19} \cdot 2 \cdot 10^4}{62.5 \cdot 10^3} = 5.1 \cdot 10^{-21} \text{ Amp}^2$$

$$i_{nT} = \sqrt{\langle i_n^2 \rangle} = 7.1 \cdot 10^{-11} \text{ Amp}$$

Shot Noise $$\langle i_n^2 \rangle = 2qBi_0; \text{ for } i_0 = 8 \, \mu A$$

$$\langle i_n^2 \rangle = 2 \cdot 1.6 \cdot 10^{-19} \times 2 \cdot 10^4 \times 8 \cdot 10^{-6} = 5.1 \cdot 10^{-20} \text{ Amp}^2$$

$$i_{ns} = \sqrt{\langle i_n^2 \rangle} = 2.3 \cdot 10^{-10} \text{ Amp}$$

1/f noise

This is caused by surface effects in MOS devices. In our case, the channel is mostly a "buried channel", due to the arsenic implant. As such, the carriers are not located directly at the surface, but somewhat deeper in the semiconductor. Furthermore, the fact that a depletion type device is used with no DC bias between the solution and the silicon, results in practically no electric field in the oxide on top of the floating gate. Consequently, tunneling currents which are known to cause 1/f noise will be absent. It is therefore expected that the 1/f noise will be low, as compared to that of a conventional MOS device. Altogether it is expected that the measured current signal of about 2.9 $\mu A$ will be much higher than the three noise sources.

The direct coupling of the neuron to the MOS transistor suffers from several drawbacks:

1) Uncontrolled distance and contact area between the two. This will affect both the coupling of the neuron action potential ($V_A$) to the MOS device, as well as the value of the shunting resistance (Rs) and the resulting signal decay time.

2) The exposure of the device to the ionic solution may cause uncontrolled ionic currents and device degradation.

3) In the case of synaptic coupling to the MOS device the signal levels can be lower by up-to two orders of magnitude. Consequently, the system may fail on the basis of signal-to-noise ratio.

In order to overcome these obstacles, the present invention incorporates molecular amplifiers (voltage-sensitive dyes) and neuro-compatible interface (peptides and disacharides) which will enhance the measured signal through different mechanisms:

a) Molecular-affinity derived coupling of neurons to the MOS transistor. Neural growth and adhesion factors will affix the neuron-membrane to the device surface.

b) Eliminating the shunting effect of the solution. The effective coupling of the neurons to the transistor and the filling of the space between the silicon top surface and the neurons by the binding moities, will remove the ionic solution from this interface.

c) Enhancement of the device sensitivity by molecular amplifiers that respond in charge-induction at the floating gate electrode.

Figure 3C:
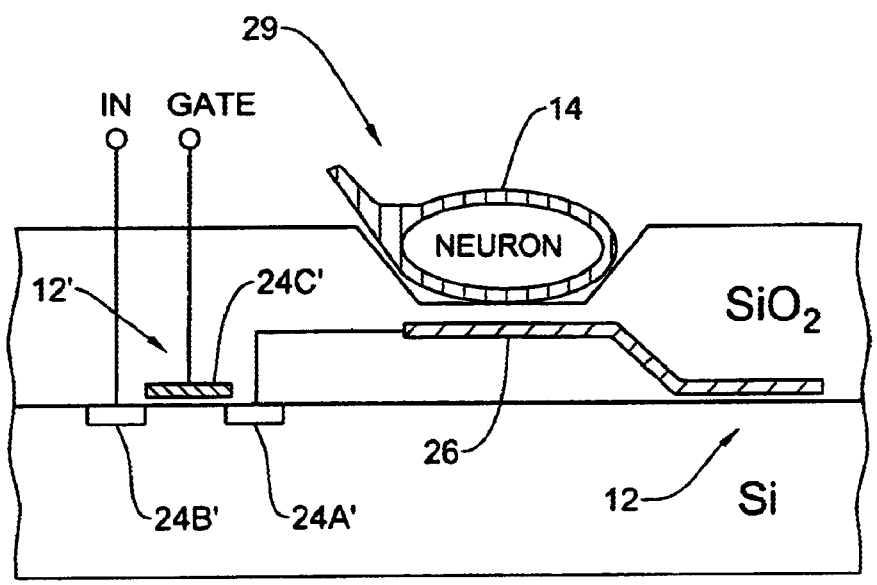
FIG. 3C schematically illustrates a device for VSC sensing and stimulation processes.

Referring to FIG. 3C, there is illustrated a device 29 according to another embodiment of the invention used for both the neuron sensing and stimulation processes. The device 29 utilizes the above-described electrical junction between the floating gate depletion type transistor 12 and the VSC 14, and an additional switching transistor 12' whose source (or drain) electrode 24A' is connected to the floating gate 26 of the transistor 12. When no voltage is supplied to the gate electrode 24C' of the switching transistor, the device 29 operates for sensing signals coming from the VSC 14 in the above-described manner. When a certain voltage is supplied to the gate electrode 24C' and a voltage pulse is applied to the input of transistor 12' (electrode 24B'), this voltage pulse will reach the VSC through the floating gate 26 of the transistor 12, thereby stimulating the VSC. Such a device can for example be used for stimulating the patient's retina with output signals indicative of an image of the surroundings. The use of a floating gate depletion type transistor with no DC bias enables the addition of the switching transistor. In a floating gate transistor of the kind, where a DC bias has to be applied, the addition of such a switching transistor would introduce a junction leakage current, which prohibits the proper use of the device.

Figure 4:
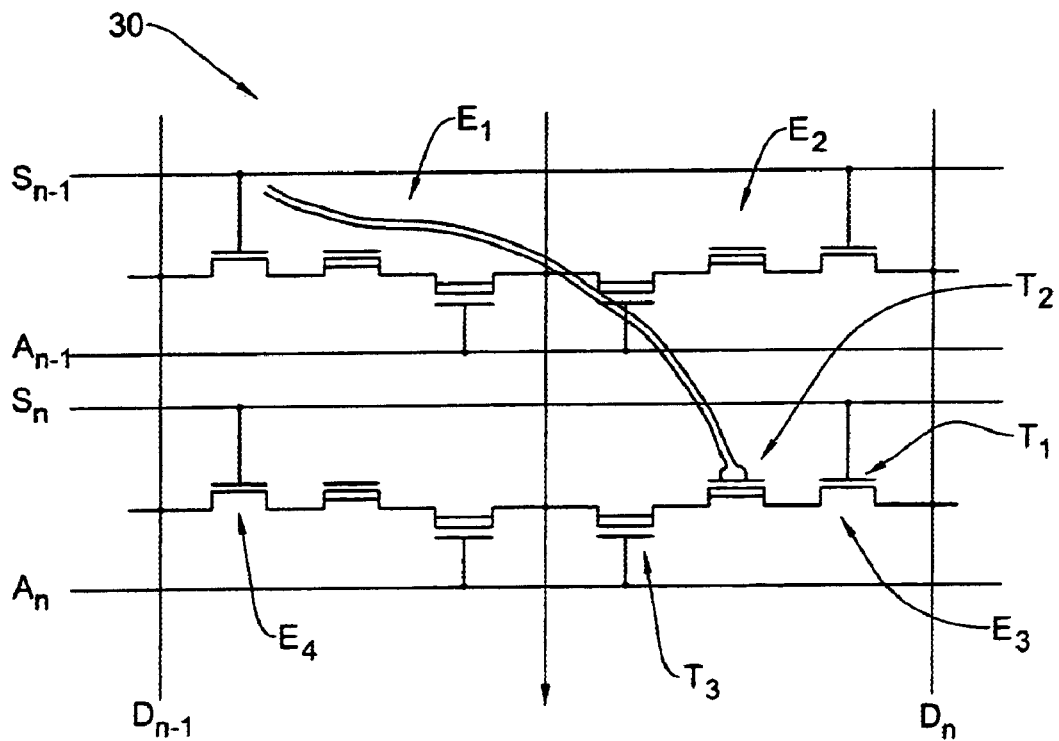
FIG. 4 illustrates one possible example of an electronic scheme utilizing the device of FIG. 2A.

Reference is now made to FIG. 4, showing an electronic scheme, generally at 30, utilizing the device of the present invention in a neuron network configuration. This is an example of a small array enabling the two-way interaction. The scheme 30 is composed of an array of four elements $E_1$–$E_4$, each comprising three transistors $T_1$–$T_3$ in series. The intermediate transistor $T_2$ is the floating gate depletion type device 12 described above with the neuron 14 on top of it's floating gate. The two transistors $T_1$ and $T_3$ are regular enhancement type devices coupled to the source and drain of the transistor $T_2$, and serve as electronic switches.

Each of the elements operates in the following manner. During the sensing stage, the transistors $T_1$ and $T_3$ are turned on by high gate voltages (input circuits $S_n$ and $A_n$ are at high voltage). Since they are much wider than the sensing transistor $T_2$, they are practically shorted, and effects produced thereby are thus negligible. The detected signal (the current flowing through the active component of the transistor $T_2$) is measured on the output $D_n$ of one of these regular type transistors.

During the stimulation stage, one of the transistors $T_1$ and $T_3$ is again shorted, while the other is in off state by applying a zero gate voltage. In the present example, the input $S_n$ of the transistor $T_1$ is at high voltage, and tie input $A_n$ of the transistor $T_3$ is at zero voltage. When a high voltage pulse is applied to the source of the shorted transistor ($T_1$), it will reach the source/drain/depletion channel of the transistor $T_2$, and consequently will activate the neuron through the capacitive coupling of the floating gate.

As further shown in FIG. 4 in dashed lines, more than one transistor can be used with a common neuron. To this end, the neuron 14, whose membrane is coupled to the floating gate depletion type transistor $T_2$ of the element $E_3$, is by its axon connected to the similar transistor of the element $E_1$.

Comparing the above scheme to that disclosed in the above-indicated article, the depletion type channel in the device of the present invention serves the same function as the p-region in the prior art device. However, according to the present invention, his p-region is not heavily doped, but lightly doped and as such that its conductivity can be modulated by the neuron action potential.

EXAMPLE 1

Silicon-based Transistor Device Fabrication

The process for fabrication of the transistor is based on eight masking steps, using the floating gate concept. It was calculated that by optimization of the device structure, it is possible to allow relatively large displacement of about several micrometers of the two elements, i.e. neuron and the channel, with no reduction in the electrical signal. For the configuration shown in FIG. 1, it was calculated that the signal will be reduced as compared to direct accurate placement of the neuron on the exposed gate oxide, by less than a factor of two. One of the advantages of embedding the floating gate in the Si oxide layer on top of which the neuron is bound via the appropriate biological binding moieties, is that the effects are averaged over the complete channel area. The only effect of the floating gate on the transistor-neuron coupling is one of change in effective dielectric thickness. Addition of gold metal layer, used for electrostatic screening of the transistor connectors from the neural system, reduces the noise to such low levels that more than compensate for the reduced signal. A minimum dimension device is used with low drain voltage to reduce power consumption resulting in reduced heating. Proper channel implant results in depletion type device capable of detecting both positive and negative neuronal signals as well as activation of the neuron by a signal applied to the channel which is capacitively coupled to the neuron.

EXAMPLE 2

GaAs-based Device Fabrication

Being a versatile substrate, GaAs permits the application of various kinds of coupling. This allows alternative chemistries to be investigated. Highly sensitive, single GaAs transistors with separate anchoring sites for binding moieties can be used to benchmark the neuro-electronic synapse on their silicon counterparts and to set an internal standard regarding noise levels. Shallow multiple quantum wells (MQW) are also used as highly sensitive affinity sensors. The adsorption of molecules onto the surface of the transistor causes a change in bandbending and in electron affinity and can also shift the fermi level. Adsorption therefore modulates the transport properties of the quantum wells. However, to this end, the fermi level has to be de-pinned first.

EXAMPLE 3

Fabrication of Arrays

Using the fact that the technology of integrated circuits allows for simultaneous fabrication of a large number of devices, an array of devices can include some switching devices which are added which allow for two way neuron-transistor interaction, i.e., the transistors will be used both for sensing neuron activity by detection of voltage changes as well as for triggering the firing of action potentials by applying voltage changes to the neurons. The use of a high density transistor array will allow also to tolerate improper alignment of the neurons to the individual transistor devices since it is relatively easy to electronically change the addressing of the devices.

Turning back to FIG. 4, showing a schematic layout of a small array enabling the two-way interaction, the preferred technology for the realization of such an array including peripheral circuitry performing wide range of electronic functions, is a modified CMOS process. By the addition of one masking step used for ion implant in the channel of the depletion type device, and by replacing the top metallization layer with gold, it will make the standard CMOS process suitable for the realization of the invention.

EXAMPLE 4

Design of Transistor Interface

For reasons clarified below, the design of the interface includes both an array of transistor interfaces and driving electronics, implemented on the same substrates. The preferred approach is similar to that of memory and imaging chips where the array is at the center of the chip and the following electronic functions are placed around the array:

- synchronous communication interface to program a decoder;
- a n-bit decoder that addresses the various neurons of the array;
- voltage and current references;
- clock signal generator;
- low noise amplifiers;
- AD converter. As will be understood the type of converter that is used depend on the size of the array, the required resolution and conversion rate and the available power budget;
- self test circuitry to verity the functionality of the electronics;
- a stimulus generator;
- logic circuitry that configures the array in measurement or stimulation mode.

The layout of the chip is of paramount importance to ensure that the circuit can be efficiently protected against the bathing fluid. Layout depends on the size of the array and the type of packaging. The functions described here above will be available in a "kitpart" version of the complete read-out chip.

II. Surface Chemistry

EXAMPLE 5

Manufacturing Strategy

Figure 5:
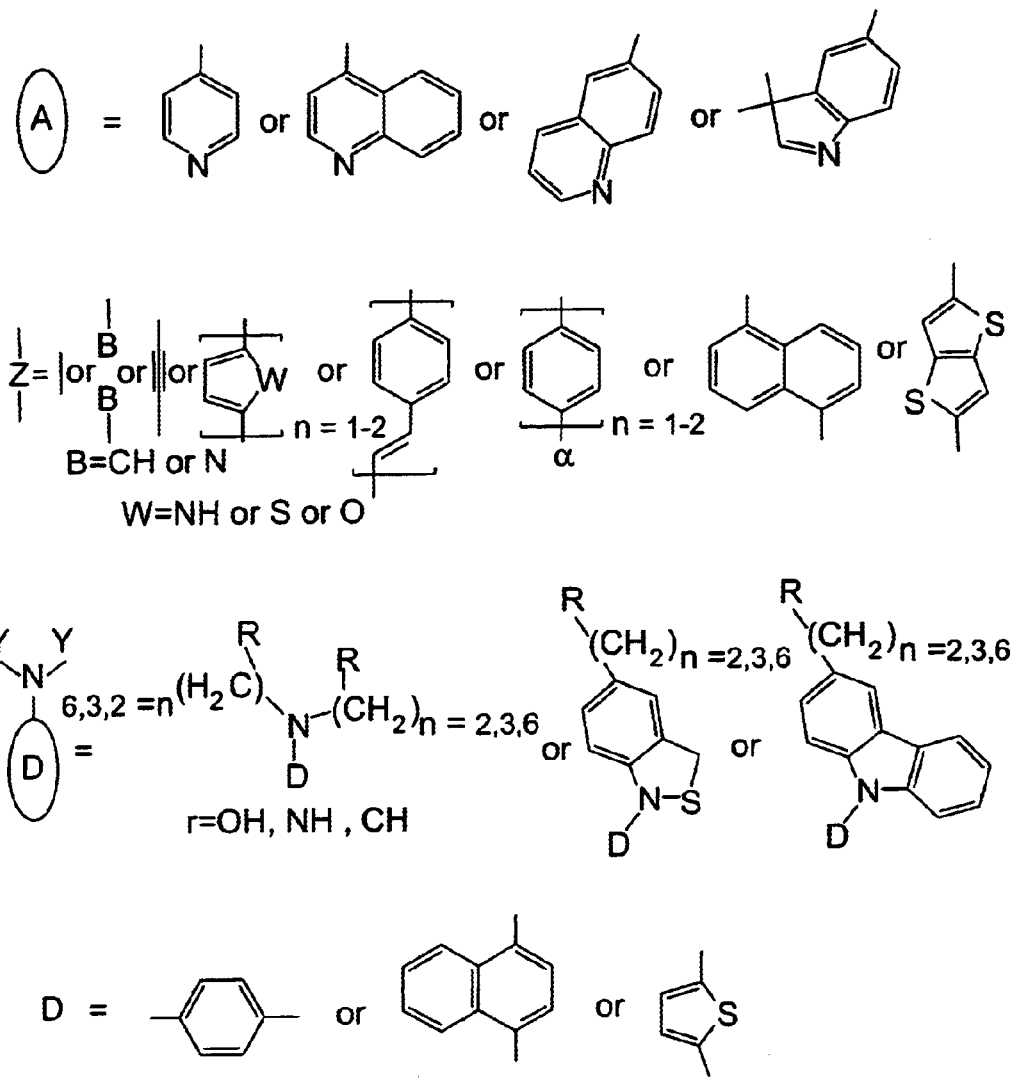
FIG. 5: (A) is a schematic demonstration of the hyper-polarizable chromophores building blocks, A—the electron acceptor part; D—the electron donor part; and Z—the bridging moiety. (B) a general formula representing hyper-polarizable chromophores.
Figure 6:
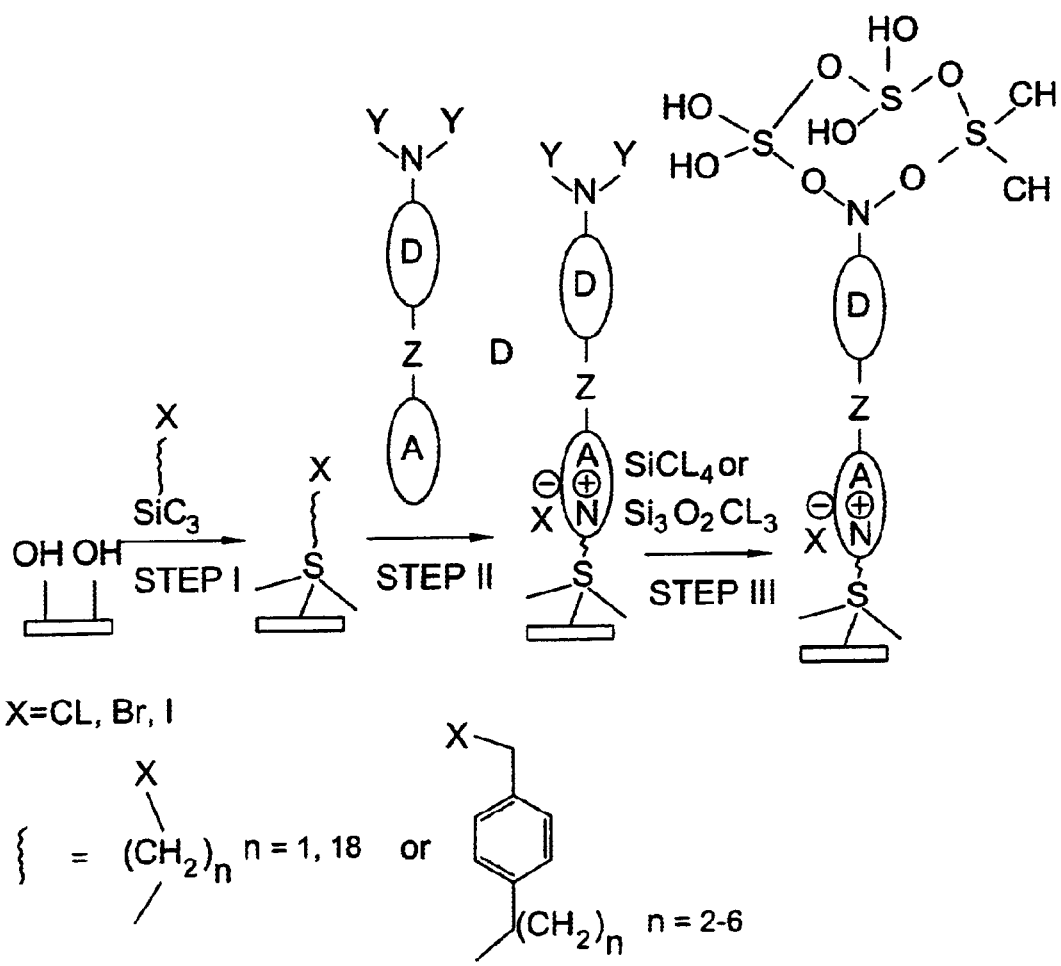
FIG. 6 illustrates the synthetic scheme for the self-assembly of a hyper-polarizable chromophore of the outer surface of a semiconductor.

The synthetic strategy for the covalent attachment of hyper-polarizable chromophore is shown in FIG. 6. In the first step (i) a $SiX_3RX$ moiety (silanizing reagent), where X is a halogen and R is a $(CH_2)_n$, n=1–18 or $(CH_2)_n$aryl, n1–6 is attached to the outer OH groups of the silicone wafer employing the trichlorosilane coupling reaction. In the second step (ii) the hyper-polarizable chromophore is anchored to the RX portion of the attached silanizing moiety. The anchoring/quaternization process converts the chromophore precursor into the highly hyper-polarizable voltage-active chromophore. Since the hyper-polarizable chromophores of the present invention may contain a hydroxyl or amino outer surface (FIG. 5), die exposed hydroxyalkyl or aminoalkyl functionalities can be subsequently used to modify the interface and further serve as basis for the construction of an additional layer. Thus in the third step (iii), an additional ion blocking network or bio-active agents such as short peptides are further attached to the exposed amino or hydroxyalkyl functionalities.

The synthetic flexibility of such monolayers is based on the fact that the cation is covalently anchored to the surface and the anion is labile and susceptible to ion exchange chemistry. The addition of an ion blocking network, generically termed as a capping reaction described in step (iii) is to prevent ion-leakage. An example of such a capping moiety is a siloxane which its exposed OH groups could further be coupled with oligosaccharides which serve as means for adhesion and fixation of a nerve cell to the device.

EXAMPLE 6

Utilizing Binding Moieties to Anchor the VSC to the Transistor (a) Short Peptides During the development of a nervous system, neurons grow by exploring their microenvironment using growth cones and form stereotype neural architecture. They selectively grow along certain pathways by recognizing specific molecular sites through their cellular receptors. Laminine, an extracellular matrix protein is known to regulate the neural adhesion and neurite outgrowth via receptor mediated interactions. Due to the fact that laminine and other proteins are large molecules (MW of about 1,000,000) the direct assembly of is protein does not assure the neurite promoting domain to face the growth surface. Thus smaller molecular weight peptides derived from the neurite promoting domains of laminine are used. Two well-studied peptides (8 and 10 amino-acids each): PA22-2 and P20-GCV may be used as well as other peptides, especially those derived from other macromolecular moieties present on the extracellular matrix or membranes which VSC's usually adhere.

Figure 7:
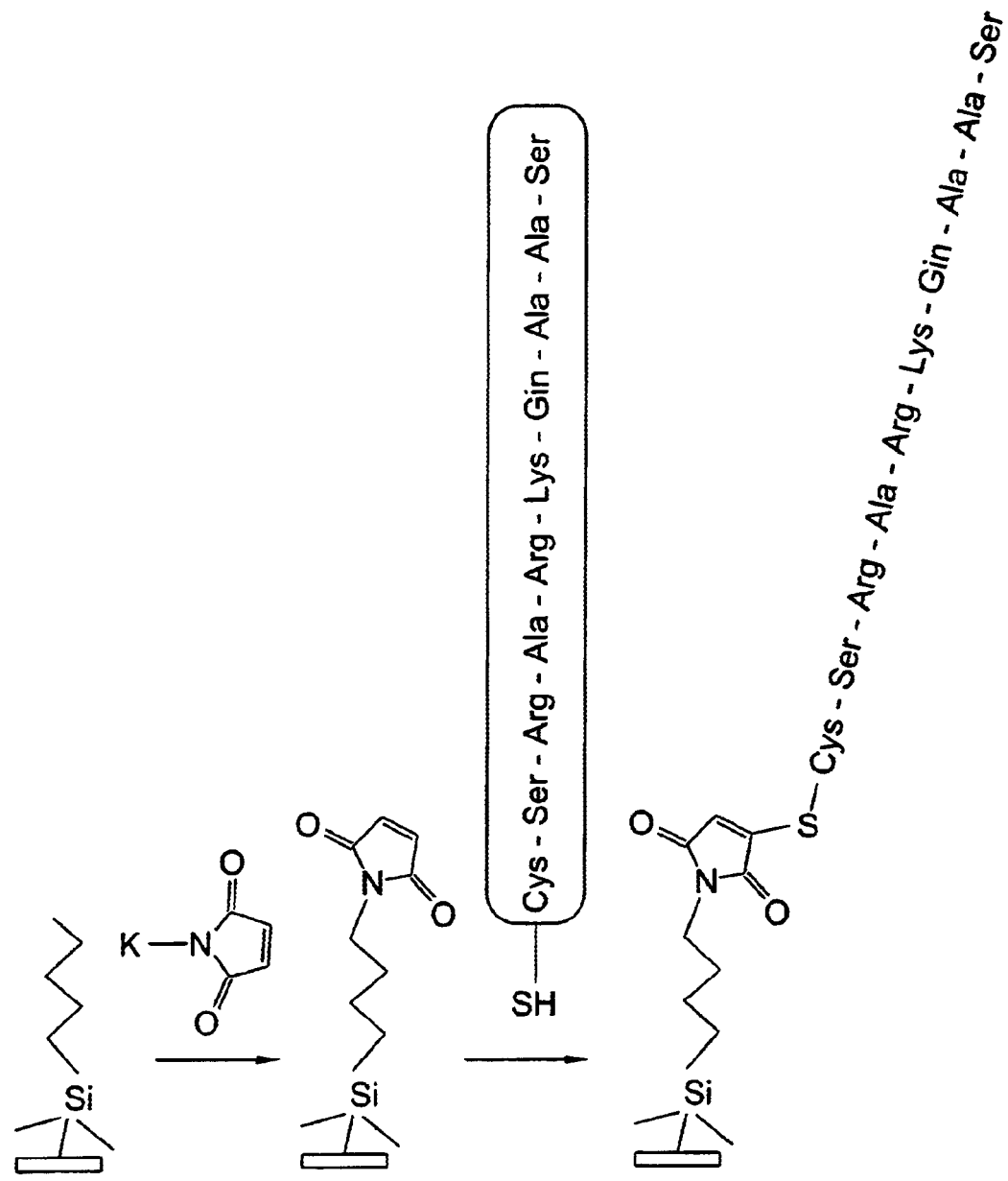
FIG. 7 illustrates the synthetic scheme for the attachment of a 10 amino acid cysteine terminated peptide to the surface of the transistor and FIG. 8 shows the change in three parameters of Electronic Properties of n-Silicon as a function of the Surface Number Densities of the Voltage-Sensitive Dye of FIG. 5.

Binding of each of these peptides is done by a different chemical route taking advantage of the terminal lysine and cysteine of the 8 and 10 amino acid peptides, respectively. FIG. 7 illustrates tie chemical route for the attachment of the cysteine-terminated peptide. Thus the peptide is anchored to the surface after an alkyl or benzyl halide is coupled to the silicone surface (step (i)) of FIG. 6. The halide is further reacted with a maleimido group which reacts with the terminal SH group of cysteine. The lysine-terminated peptide is coupled to the alkyl or benzyl halide via a schiff-base reaction of a gluteraldehyde which serves as a bridge between the halide and the lysine $NH_2$ group.

(b) Oligosaccharide and Branched Hydrocarbons

One of the most serious problems is the poor adhesion of the nerve-cells to the transistor is the solution-derived shunting noise. This obstacle is overcome by the creation of intimate neuron-silicon contacts. Hyaluronan, the polysaccharide part of proteoglycan in the extracellular matrix, facilitate cell migration during tissue morphogenesis and repair. The glycosaminoglycan repeating unit can be easily inserted via ether linkages to the chromophoric layer on top of the capping layer, see Scheme V.

EXAMPLE 7

Electronic Effects of Adsorbed Molecules on Transistor

The fundamental action of monolayers absorbed on the semiconductor is studied using C-V measurements and Contact Potential Difference (CPD) measurements using the Kelvin probe technique. The band bending can be estimated from the difference in the semiconductor work-function Φ before and after illumination (photosaturation), ref. 12. From the relation, $\Delta\Phi=\Delta\chi+\Delta V_{bb}$ and the measured values of $\Delta\Phi$ and $\Delta V_{bb}$, the change in the electron affinity, $\Delta\chi$, can be calculated. C-V measurements with semitransparent top electrode also provide information on changes of band-bending and electron-affinity. Surface photovoltage spectroscopy (CPD as function of excitation wavelength) provide qualitative information on surface state densities, especially in how far these changes in response to exposure of the adsorbed molecules to a specific chemical. In the present case this can be due also to one of the membrane proteins of the nerve cell.

Figure 8:
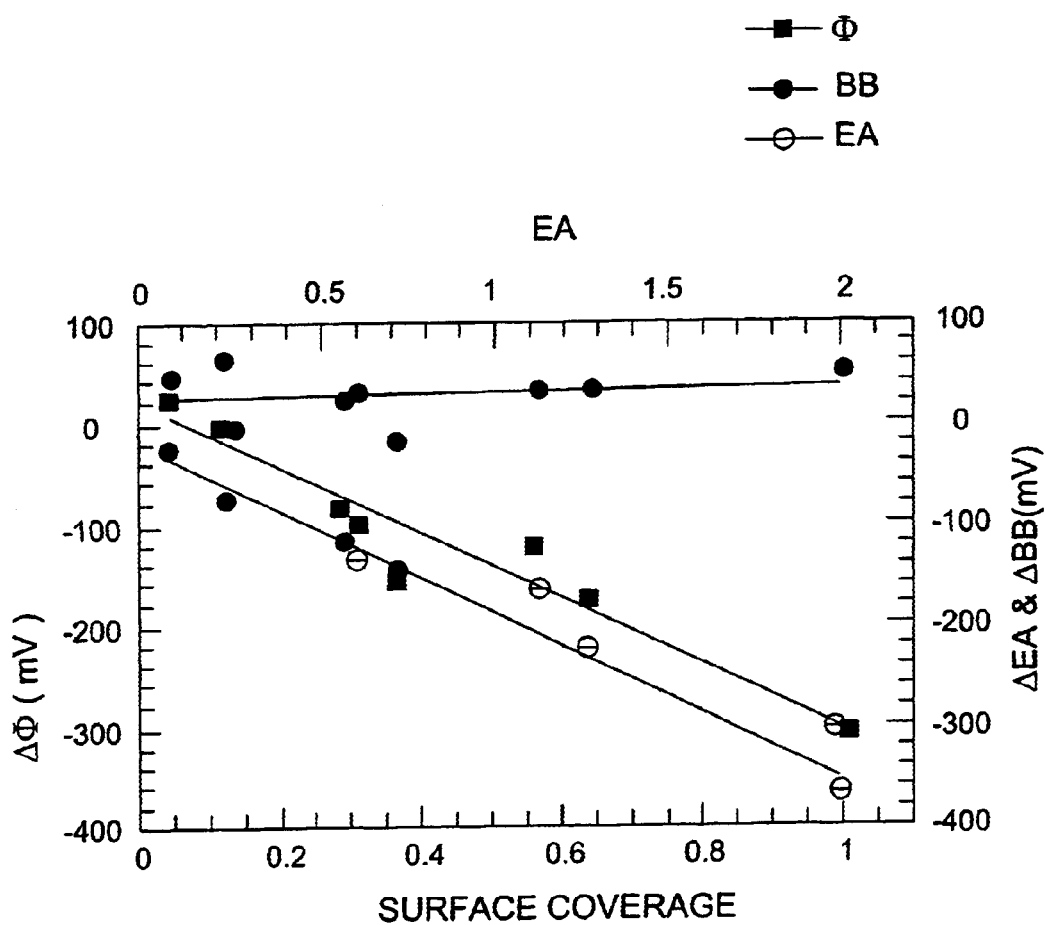

Reference is made to FIG. 8 which demonstrates a large molecular electronic effect of chromophore shown in FIG. 5 self-assembled on Si as measured by CPD. Three graphs are shown corresponding, respectively, to the changes in the semiconductor work-function $\Delta\Phi$ (Φ), electron affinity $\Delta\chi$ (EA) and band bending $\Delta V_{bb}$ (BB) as functions of the density of the voltage sensitive dye P-dialkyl-amino ozobenzene pyridinum on the n-Si wafer.

As shown, the large observed changes in silicon's work-function (ca. −400 mV) is directly proportional to the chromophore number density that is grafted on the Si-wafer. Similar changes in the effective dipole and charge distribution of the monolayer interfacing neuron/MOS device are expected to take place upon neural action potential.

EXAMPLE 8

Surface Patterning of an Electrochemical Junction

In order to form spatially defined organic surfaces with voltage-sensitive dyes and/or synthetic peptides deep UV lithography technique with self-assembled monolayers is used [Ref. 7] This method already proved useful in micropatterning of glass substrates with OTS/amine domains followed by synthetic peptide assembly and neuron growth.
III. Neurobiology

EXAMPLE 9

Molecules that Determine the Growth Directionality of VSC

Neuron growth is mediated by a plurality of growth promotive and growth repulsive molecules. This property can be used to direct the growth of the neuron (VSC) to the transistor both for the production of the electrical and of the electrochemical junction of the invention.

This will be done by patterning the surfaces of the transistor by alternating micro-strips of growth promoting molecules (for example polylysine) and repulsive molecules such as colapsin which rapidly suppress actin-based motility in the growth cone. These molecules direct the growth of the neurons to the junction. These molecules also provide stability and reduce the space between the neuronal membrane and the silicon surface and in fact serve as binding moieties. There are two distinct classes of cell to cell adhesion molecules which are used as binding moieties where the VSC is a neuron. The calcium dependent and the calcium independent CAMs (cadherins). The CAMs are single-pass transmembrane glycoproteins composed of 700–750 amino acid residues. The formulation of these bindings, determine the space between cells and the transistor. Some cadherins (such as integrins) mediate (by heterophilic interactions) the attachment of cells membrane to the extracellular matrix (the substrate to which the cell adheres to). The second type of adhesion molecules are the calcium independent molecules belonging to the immunoglobulin (Ig) supper family of proteins. N-CAMs, as cadherins, form homophilic or heterophilc links with adjacent cells and substrates. The effects of the molecules on the electrical coupling of the hybrid is tested by electrophysiological techniques see (c) below. Molecular signals that provide a stop sign to the extending growth cones. For example agrin and s- laminine provide the "stop sign" in vertebrate neuromuscular synapse. In Aplysia ApCam an Aplysia adhesion molecule related to vertebrate NCAM and Drosophila FasciculinII induces chemical synapses formation in the form of verecosities.

EXAMPLE 10

Biocompatibility Results

Glass interfaces self-assembled with voltage sensitive dyes were fabricated and used as a growth substrate Aplysia neurons. The neurons successfully grew on such chemically modified interfaces with no adhesion problems demonstrating a fundamental biocompatibility of such chemically modified interfaces for neural growth.

IV. Electrochemical Junction (Artificial Synapase)

The functional assay of this electrochemical junction is done in two stages:

(a) The function of the artificial post synaptic chemical component is evaluated by local iontophoretic application of Ach through a microelectrode. Such an application mimics the release, of ACh by the nerve terminal.

(b) Neurons are then cultured on the electrical device and stimulate the pre synaptic neuron and that the current generated by the post synaptic electrical device is measured.

What is claimed is:

1. An electrical junction between one transistor and at least one voltage-sensitive cell (VSC) characterized by at least one of the following features:

(a) voltage transfer between the transistor and the VSC is bi-directional, the transistor being a floating gate depletion type device, the VSC being connected to a floating gate electrode of the transistor and being capable of being stimulated by a voltage pulse applied to the source, channel and drain of the transistor;

(b) there is no DC bias voltage between the transistor and a biological solution in which the VSC is embedded, the transistor being a depletion type device;

(c) the VSC is anchored to an external surface of the transistor by binding moieties, optionally through spacers; and (d) the voltage transfer between a membrane of the VSC and an external surface of the transistor, and between the external surface of the transistor and the membrane of the VSC is mediated by hyper-polarizable chromophores.

2. A junction according to claim 1, wherein the transistor is a structure fabricated by a semiconductor-based integrated technology.

3. An electrical junction according to claim 2, wherein the floating gate electrode is shaped such that its one portion is accommodated in an active area formed in a semiconductor substrate of the transistor to define an active component of the transistor, and its other portion is accommodated outside said active area defining a site for the VSC accommodation.

4. An electrical junction according to claim 3, wherein the transistor comprises a screening metallization layer accommodated in the vicinity of the active area.

5. An electrical junction according to claim 4, wherein said screening metallization layer is metal of lower chemical activity than the commonly used aluminum.

6. An electrical junction according to claim 5, wherein said metal is gold.

7. An electrical junction according to claim 2, wherein said transistor is a Si-based structure.

8. An electrical junction according to claim 2, wherein said transistor is a GaAs-based structures.

9. A device for detecting voltage changes from a plurality of voltage-sensitive cells (VSCs) and/or for transfer of voltage changes to a plurality of VSCs, the device comprising an array of transistor elements, each transistor element being independently operable and comprising a floating gate depletion type transistor in voltage transfer association with the VSC, thereby forming the junction of claim 1, and two regular type transistors coupled to source and drain electrodes, respectively, of said floating gate depletion type transistor.

10. A junction according to claim 1 (iii), wherein the binding moieties are proteins, polypeptides, peptides or lectins attached to the external surface of the transistor and capable of binding to membranal components present on the membrane of the VSC.

11. A junction according to claim 10, wherein the binding moieties are selected from the group consisting of: antibodies, receptors, ligands, lectins and adhesion molecules.

12. An electrical junction according to claim 1, characterized by a combination of features (i), (ii), (iii) and (iv).

13. An electrical junction between one transistor and at least one voltage-sensitive cell (VSC) characterized by bi-directional voltage transfer between the transistor and the VSC, the transistor being a floating gate depletion type device, the VSC being associated with a floating gate electrode of the transistor and being capable of being stimulated by a voltage pulse applied to the source, channel and drain of the transistor.

14. An electrical junction between one transistor and at least one voltage-sensitive cell (VSC) characterized by no DC bias voltage between the transistor and a biological solution in which the VSC is embedded, the transistor being a depletion type device.

15. A device for selectively detecting voltage changes in a voltage-sensitive cell (VSC) and transferring voltage changes to the VSC, the device comprising:
   an electrical junction between a floating gate depletion type transistor and the VSC, the VSC being connected to a floating gate electrode of the transistor and being capable of being stimulated by a voltage pulse applied to the gate electrode of the floating gate transistor; and
   a switching transistor connected by either one of its source and drain electrodes to the gate electrode of said floating gate transistor to apply said voltage pulse by supplying voltage to a gate of the switching transistor.

16. A device according to claim 15 characterized in that the VSC is anchored to an external surface of the transistor by binding moieties, optionally through spacers.

17. A device according to claim 16, characterized in that the voltage transfer between a membrane of the VSC and the external surface of the transistor, and between the external surface of the transistor and the membrane of the VSC is mediated by hyper-polarizable chromophores.

18. A device according to claim 15, characterized in that the voltage transfer between a membrane of the VSC and the external surface of the transistor, and between the external surface of the transistor and the membrane of the VSC is mediated by hyper-polarizable chromophores.

19. A device for detecting voltage changes in at least one voltage-sensitive cell (VSC) and/or for transfer of voltage changes to at least one VSC comprising: the junction of claim 1, wherein a floating gate electrode of the transistor is electrically connectable to said at least one VSC within an area outside an active area defined by a location of an active component of the transistor.

20. A device according to claim 19, wherein the electrical connection is capacitance-based connection.

21. A device according to claim 19, wherein said transistor is a depletion type device, the electrical connection being bi-directional.

22. A floating gate transistor to be used in a hybrid device for communicating with a voltage-sensitive cell (VSC), the transistor having an active area defined by a location of an component of the transistor, and having source and drain electrodes making contacts to the active component and a floating gate electrode, the floating gate electrode having its first portion insulated from the active component and accommodated in the vicinity of the active area thereabove, and a second portion accommodated outside said active area and being displaced therefrom in a plane defined by the active component, said second portion defining a site for the VSC accommodation.

23. A transistor according to claim 22, further comprising a screening metallization layer accommodated in the vicinity of the active area.

24. A transistor according to claim 22, further comprising binding moieties located on its external surface within said site.

25. A transistor according to claim 24, wherein the binding moieties are proteins, polypetides, peptides or lectins attached to the external surface of the transistor and capable of binding with membranal components present on the membrane of the VSC.

26. A transistor according to claim 25, wherein the binding moieties are selected from the group consisting of: antibodies, receptors, ligands, lectins and adhesion molecules.

27. A method for the production of the transistor of claim 24, comprising:
   coating an outer layer of the transistor with a monolayer of $SiX_3RX$ moiety, where X is a halogen and R is a $(CH_2)_n$ n=1–18 or $(CH_2)_n$ aryl, n=1–6 group thus forming a halogen terminated monolayer;
   optionally converting said terminal halogen to another chemical reactive moiety such as amine, maleimide, succinimide or hydroxyl;
   reacting said chemical reactive terminated monolayer with the binding moiety under conditions enabling formation of a covalent binding between the binding moiety and the halogen.

28. A junction according to claim 1 (iv), wherein the hyper-polarizable chromophore is of the general structure A—Z—D, wherein:
   A is a mono, bi or tricyclic heteroaryl moiety;
   Z is a π-bridging moiety chosen from y=y, wherein y is CH or N; alkyne, furan, thiophene, pyrole, styrene, phenyl, biphenyl;
   D is B—$NR_1R_2$ wherein B is a phenyl, biphenyl or thiophene;
   $R_1$ and $R_2$, which may be the same or different, are $(CH2)_n$—R, R being an amino, hydroxyl or a lower alkyl, or $R_1$ and $R_2$ may be part of a polycyclic heteroaryl system.

29. A junction according to claim 28, wherein the hyper-polyrizable chromophore is selected from the following: azobenzene dyes, stylbene dyes, azomethyne dyes, cyanine, hemicyanine, merocyanine, stylbene, azobenzene, [5-(1-methyl-thiazolidene-2-ylidene) ethylene]-4-oxo-2-thioxo-thiazolidene3-5-(4-dimethyylacid sodium salt (MMT) 5-(4-Dimethylamino-benzylidene)-rodanine (DBR), thiazolidenes and rodanines.

30. A transistor having its external surface carrying hyper-polarizable chromophores.

31. A transistor according to claim 30, wherein the hyper-polarizable chromophores are of varying lengths.

32. A transistor according to claim 30, wherein the hyper-polarizable chromophores are attached to spacers of varying lengths.

33. A transistor according to claim 32, wherein the lengths of the spacers vary between 1 nm to 30 nm.

34. A transistor according to claim 32, wherein the spacers are selected from the group consisting of: oligosaccharides, straight and branched hydrocarbon, polymers and heteroatom containing molecules.

35. A method for the production of the transistor of claim 30, comprising:

coating an outer layer of the transistor with a monolayer of $SiX_3RX$ moiety, where X is a halogen and R is a $(CH_2)_n$ n=1–18 or $(CH_2)_n$ aryl, n=1–6 group thus forming a halogen terminated monolayer;

reacting said halogen terminated monolayer with a hyper-polarizable chromophore or chromophore precursor; and optionally further attaching to the outer layer of the hyper-polarizable chromophore a siloxane derivative or a peptide having 5–20 amino acids.

36. An electrochemical junction between an agent-secreting cell and a transistor comprising:

an agent-secreting region of the cell positioned at an orientation enabling transfer of the agent to a location on the surface of the transistor, said location carrying recognition moieties capable of affinity binding to said agents; said binding between the recognition moiety and the agent causing the modulation of at least one electronic property of the transistor; said location further comprising catalytic moieties capable of degradation of said agent.

37. An electrochemical junction according to claim 36, wherein the electronic to property is capacitance.

38. An electrochemical junction according to claim 36, wherein the electronic property is change in dipole moment.

39. An electrochemical junction according to claim 36, wherein the cell is a neuron, the secreted agent is a neurotransmitter and the agent secreting region of the cell is the pre-synaptic region of the neuron.

40. An electrochemical junction according to claim 39, wherein the neurotransistor is acetyl choline (ACh) and the catalytic moiety is acetyl choline esterase (AChE).

* * * * *